(12) United States Patent
Bharat

(10) Patent No.: US 11,413,475 B2
(45) Date of Patent: Aug. 16, 2022

(54) ELASTICITY IMAGING-BASED METHODS FOR IMPROVED GATING EFFICIENCY AND DYNAMIC MARGIN ADJUSTMENT IN RADIATION THERAPY

(71) Applicant: KONINKLIJKE PHILIPS N.V., Eindhoven (NL)

(72) Inventor: Shyam Bharat, Arlington, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 297 days.

(21) Appl. No.: 16/558,936

(22) Filed: Sep. 3, 2019

(65) Prior Publication Data
US 2020/0001114 A1 Jan. 2, 2020

Related U.S. Application Data

(63) Continuation of application No. 14/400,115, filed as application No. PCT/IB2013/054402 on May 28, 2013, now Pat. No. 10,426,975.

(Continued)

(51) Int. Cl.
*A61N 5/10* (2006.01)
*A61B 8/08* (2006.01)
(Continued)

(52) U.S. Cl.
CPC ............ *A61N 5/1039* (2013.01); *A61B 8/466* (2013.01); *A61B 8/483* (2013.01); *A61B 8/485* (2013.01); *A61B 18/18* (2013.01); *A61N 5/1001* (2013.01); *A61N 5/1037* (2013.01); *A61N 5/1049* (2013.01); *A61N 5/1067* (2013.01);
(Continued)

(58) Field of Classification Search
CPC .......... A61B 18/18; A61B 2018/00577; A61B 2018/1807; A61B 8/466; A61B 8/483; A61B 8/485; A61N 2005/1058; A61N 5/1001; A61N 5/1037; A61N 5/1039; A61N 5/1049; A61N 5/1067; A61N 5/1077; A61N 7/02
See application file for complete search history.

(56) References Cited

U.S. PATENT DOCUMENTS 6,796,943 B2    9/2004   Mochizuki
7,914,456 B2    3/2011   Osaka
(Continued)

OTHER PUBLICATIONS

Garra, B.S. Elastography Current Status, Future Prospects, and Making it Work for you; 2011, Ultrasound Quarterly, vol. 27, No. 3, pp. 177-186.

(Continued)

*Primary Examiner* — Mark D Remaly

(57) ABSTRACT

A therapy planning system (10) includes at least one processor (74, 72) programmed to receive an initial elasticity image of the target generated prior to execution of a fraction of a treatment plan for the target. The target is delineated in the initial elasticity image to segment the initial elasticity image. One or more elasticity images of the target generated during and/or after execution of the fraction are received and delineated to segment the elasticity images. The segmentation of the initial elasticity image is compared against the segmentations of the additional elasticity images to identify motion of the target and/or changes of the target. Based on the comparison, the treatment plan is updated and/or execution of the fraction is controlled.

13 Claims, 2 Drawing Sheets

Related U.S. Application Data

(60) Provisional application No. 61/652,471, filed on May 29, 2012.

(51) Int. Cl.
*A61B 8/00* (2006.01)
*A61B 18/18* (2006.01)
*A61N 7/02* (2006.01)
*A61B 18/00* (2006.01)

(52) U.S. Cl.
CPC .. *A61N 5/1077* (2013.01); *A61B 2018/00577* (2013.01); *A61B 2018/1807* (2013.01); *A61N 7/02* (2013.01); *A61N 2005/1058* (2013.01)

(56) References Cited

U.S. PATENT DOCUMENTS

| | | |
|---|---|---|
| 2005/0267368 A1 | 12/2005 | Boctor |
| 2008/0232660 A1 | 9/2008 | Hyun |
| 2010/0081971 A1 | 4/2010 | Allison |
| 2010/0317971 A1 | 12/2010 | Fan |
| 2011/0060222 A1 | 3/2011 | Thittai |
| 2011/0080990 A1 | 4/2011 | Filiberti |

OTHER PUBLICATIONS

Schlosser, J. et al, Telerobotic System Concept for Real-Time Soft-Tissue Imaging during Radiotherapy beam Delivery, Med. Phys., vol. 37, No. 12, pp. 6357-6367, 2010.
Venkatesh, S.K. et al MR Elastography of Liver Tumors: Preliminary Results; 2008, American Journal of Roentgenology;, vol. 190, No. 6, pp. 1534-1540.

ELASTICITY IMAGING-BASED METHODS FOR IMPROVED GATING EFFICIENCY AND DYNAMIC MARGIN ADJUSTMENT IN RADIATION THERAPY

CROSS-REFERENCE TO PRIOR APPLICATIONS

This application is a Continuation Application of application Ser. No. 14/400,115, filed on Nov. 10, 2014, which is the U.S. National Phase Application under 35 U.S.C. § 371 of International Application No. PCT/IB2013/054402, filed on May 28, 2013, which claims the benefit of U.S. Provisional Patent Application No. 61/652,471, filed on May 29, 2012. These applications are hereby incorporated by reference herein.

The present application relates generally to radiation therapy. It finds particular application in conjunction with radiation beam gating and dynamic margin adjustment and will be described with particular reference thereto. However, it is to be understood that it also finds application in other usage scenarios and is not necessarily limited to the aforementioned application.

In radiation therapy, spatially targeted doses of radiation are applied to a target, such as tumors, containing cancerous or malignant tissue of a patient. Growing and rapidly multiplying cancer cells tend to be more susceptible to damage from radiation, as compared with normal cells, such that dosages administrated by proper planning preferentially kill cancerous or malignant tissue. Current clinical workflow in radiation therapy typically involves the use of a three-dimensional image to develop a treatment plan, the treatment plan including a planning target volume (PTV), margins around the target, and a plurality of fractions, each fraction specifying beam directions and energies for treating the target.

One challenge for radiation therapy is interfraction motion (i.e., motion between fractions) and intrafraction motion (i.e., motion during fractions), such as respiratory and cardiac motion. Ideally, the entire dose for a treatment plan is delivered to the target and no dose is delivered in surrounding normal tissue and/or organs at risk. However, due to interfraction and intrafraction motion, this is typically not possible and deviations between the radiation dose delivered to the patient and the planned radiation dose are common.

To address the effects of interfraction and intrafraction motion, treatment plans typically include margins around the target to ensure the target is fully irradiated. However, the addition of margins leads to the irradiation of normal tissue and/or organs at risk (OARs) proximate the target. Further, the margins are typically generic to a patient population. That is to say, the margins are typically not specific to the patient. This can lead to further irradiation of normal tissue and/or OARs proximate the target.

Additionally, gating is commonly used in radiation therapy delivery protocols to address the effects of interfraction and intrafraction motion. Gating stops delivery of radiation to the target when the target moves out of alignment with the PTV of the treatment plan. Typically, one or more external surrogates for the target (e.g., skin markers, bee bees, etc.) are employed to monitor the motion of the target. However, recent research has demonstrated the feasibility of monitoring the motion of internal surrogates for the target (e.g., markers implanted within the patient close to the target) using telerobotic ultrasound (US) imaging.

Telerobotic US imaging uses a robotic manipulator to control the pitch and pressure of an abdominal US transducer and to avoid obstructing the radiation beam with the US transducer. The treatment plan can also be designed to avoid beam directions that contain the US transducer. The dosage volume histograms (DVHs) resulting from such customized treatment plans are virtually identical to the DVHs resulting from standard treatment plans (i.e., treatment plans without restrictions on beam directions). Further, even if standard treatment plans are employed, it has been shown that the dose delivered is not significantly affected by the US transducer. The functioning of the US system is also unaffected by the beam.

While telerobotic US imaging for gating represents a significant advancement towards live volumetric target imaging, it still requires the use of internal surrogates (as opposed to using the target itself) due to inherent problems of US. Namely, the specular nature of US and the similar echogenecity levels of many tumors and surrounding normal tissue may cause difficulty in demarcating the target on conventional brightness mode (B-mode) US images. The present application provides a new and improved system and method which overcome the above-referenced problems and others.

In accordance with one aspect, a therapy planning system is provided. The therapy system includes at least one processor programmed to receive initial elasticity data indicative of a location of the target generated prior to execution of a fraction of a treatment plan for the target. Further, additional elasticity data indicative of a location of the target generated during and/or after execution of the fraction is received. The initial elasticity data and the additional elasticity data are compared to identify motion of the target and/or changes of the target. Based on the comparison, the treatment plan is updated and/or execution of the fraction is controlled.

In accordance with another aspect, a therapy planning method is provided. The therapy method includes receiving initial elasticity data indicative of a location of the target generated prior to execution of a fraction of a treatment plan for the target. Further, additional elasticity data indicative of a location of the target generated during and/or after execution of the fraction is received. The initial elasticity data and the additional elasticity data are compared to identify motion of the target and/or changes of the target. Based on the comparison, the treatment plan is updated and/or execution of the fraction is controlled.

In accordance with another aspect, a therapy planning system is provided. The therapy system includes at least one processor programmed to receive elasticity images of the target in real-time during execution of a fraction of a treatment plan for the target. The target is delineated in the received elasticity images to segment the elasticity images. A reference segmentation is compared against the segmentations of the elasticity images to identify motion of the target and/or changes of the target. The reference segmentation delineates the target in an elasticity image. Based on the comparison, the treatment plan is updated and/or execution of the fraction is controlled.

One advantage resides in directly monitoring motion of the target with ultrasound.

Another advantage resides in gating based on positional information obtained directly from the target.

Another advantage resides in direct visualization of radiation-related changes to the target.

Another advantage resides in the use of elasticity (or strain) images.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
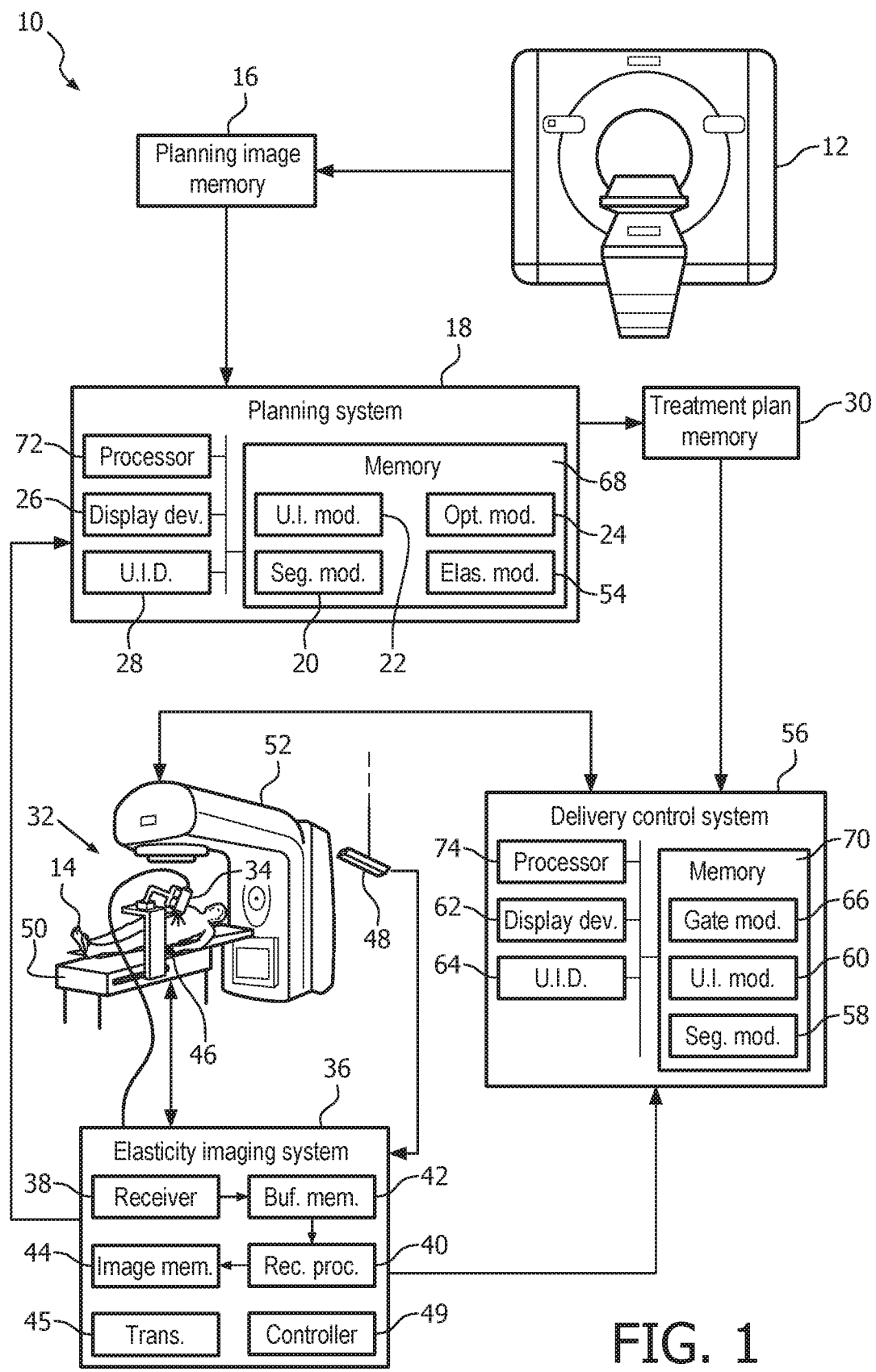
FIG. 1 illustrates a block diagram of a therapy system for treating a target of a patient.

With reference to FIG. 1, a therapy system 10 includes a planning imaging modality 12 generating a planning image, such as a three-dimensional image, of a target and, commonly, one or more organs at risk (OARs) of a patient 14. The target is an organ or other tissue region which contains a lesion, such as a tumor, to be treated. The planning imaging modality 12 is suitably one or more of a computed tomography (CT) scanner, a positron emission tomography (PET) scanner, a magnetic resonance (MR) scanner, a single photon emission computed tomography (SPECT) scanner, a cone-beam computed tomography (CBCT) scanner, and the like. The generated planning image is typically stored in a planning image memory 16 of the therapy system 10.

A planning system 18 of the therapy system 10 receives the planning image from the planning imaging modality 12, typically via the planning image memory 16. Using the planning image, the planning system 18 generates and/or updates a treatment plan for the patient 14. As to the former, the planning image is generated prior to therapy delivery. As to the latter, the planning image is typically generated between fractions, such as, for example, after a predetermined number of fractions have been completed. To facilitate planning, the planning system 18 includes one or more of a segmentation module 20, a user interface module 22, and an optimization module 24.

The segmentation module 20 receives an image, such as the planning image, and delineates one or more regions of the image, such as the target and/or the OARs. The regions are typically delineated with contour(s) tracing the boundaries of the regions in the image. Delineation can be performed automatically and/or manually. As to automatic delineation, any number of known segmentation algorithms can be employed. As to manual delineation, the segmentation module 20 cooperates with the user interface module 22 to allow clinicians to manually delineate the regions in the image and/or manually adjust automatic delineations of the regions in the image.

The user interface module 22 presents a user interface to an associated user with a display device 26 of the planning system 18. The user interface can allow the user to at least one of delineate regions of an image, modify delineations of regions of an image, and view delineations of regions of an image. Typically, the user delineates a region of an image by drawing a contour along the boundary of the region on the image using a user input device 28 of the planning system 18. Further, a delineation of a region in an image is typically viewed by overlaying a representative contour on the image, and modified by resizing and/or reshaping the representative contour using the user input device 28. The user interface can also allow the user to enter and/or define parameters for generating and/or updating the treatment plan using the user input device 28.

The optimization module 24 receives plan parameters for the treatment plan, typically from the user interface module 22, as well as contours delineating the target and/or the OARs in the planning image from the segmentation module 20. The optimization module 24 can also receive other relevant inputs, such as a delivered dose distribution indicating dose delivered to the target. Based on the plan parameters, the contours and any other relevant inputs, the optimization module 24 generates and/or updates the treatment plan so it complies with the plan parameters. The treatment plan suitably includes a planning target volume (PTV), margins around the target, and a plurality of fractions, each fraction specifying beam directions and energies for treating the target. The treatment plan generated by the optimization module 24 is suitably stored in a treatment plan memory 30.

The therapy system 10 further includes an elasticity imaging modality 32 generating one or more elasticity (or strain) images of the target and/or the OARs. The elasticity images are typically three dimensional images, but two dimensional images are also contemplated. Elasticity images provide information on size and boundary of the target and/or the OARs that may not be available in other types of images. Namely, the target may be differentiable from surrounding normal tissue with higher contrast, depending on the underlying mechanical properties of the target. For example, malignant liver tumors are known to be significantly stiffer (approximately 10 kilopascals) than normal liver tissue (e.g., approximately 2 kilopascals).

The elasticity imaging modality 32 is typically an ultrasound (US) imaging modality (as illustrated), but other types of imaging modalities capable of generating elasticity images, such as an MR imaging modality, are contemplated. Further, it is to be appreciated that the elasticity imaging modality 32, typically, also generates other types of images. For example, where the elasticity imaging modality 32 is a US imaging modality, the elasticity imaging modality 32 can also generate brightness mode (B-mode) images. Even more, the elasticity imaging modality 32 and the planning imaging modality 12 can be one and the same. However, for ease of discussion, the elasticity imaging modality 32 and the planning imaging modality 12 are described separately.

To generate the elasticity images, a sensing device 34, such as a US transducer, of the elasticity imaging modality 32 generates spatially encoded data representing sensed elasticity properties of the target and/or the OARs. The spatially encoded data is typically generated during therapy delivery (i.e., execution of the treatment plan), but can also be generated before therapy delivery and/or after therapy delivery.

An elasticity imaging system 36 of the elasticity imaging modality 32 acquires the spatially encoded data from the sensing device 34, using, for example, a receiver 38, and processes the spatially encoded data into the elasticity images. The processing includes reconstructing the spatially encoded data into the elasticity images, using, for example, a reconstruction processor 40 of the elasticity imaging system 36, and varies depending upon the sensing device 34. The elasticity imaging system 36 processes the spatially encoded data in real-time as it is generated, but could generate elasticity images at a later time. Typically, the spatially encoded data and/or the elasticity images are stored in a data buffer memory 42 and an elasticity image memory or buffer 44, respectively, of the elasticity imaging system 36. The elasticity imaging system 36 further transmits excitation signals, such as radio frequency signals, into the target and/or the OARs to prompt generation of the spatially encoded data. The excitation signals can be transmitted, for example, using a transmitter 45 and/or the sensing device 34.

When the sensing device 34 is a US transducer, the sensing device 34 can take a variety of forms. According to one form, the sensing device 34 is formed of a one dimensional array of transducer elements generating the spatially encoded echo data. Such a sensing device is mechanically moved to generate spatially encoded data for identifying a current location of the target or the OARs (e.g., with a three dimensional image). Further, such a sensing device can be positioned at a fixed position to generate spatially encoded data for a two dimensional image. According to another form, the sensing device 34 is formed of a two dimensional array of transducer elements generating the spatially encoded data. Such a sensing device can be positioned at a fixed position and electronically swept to generate spatially encoded data for a two or three dimensional image or other indicator of location or distance.

A sensor-positioning device 46 of the elasticity imaging modality 32 moves the sensing device 34. Typically, the sensor-positioning device 46 is a robotic arm (as illustrated), but other mechanical devices for positioning and/or moving the sensing device 34 are contemplated. The sensor-positioning device 46 is only necessary to the extent that the sensing device 34 needs to be moved to generate the elasticity images. For example, as noted above, the sensing device 34 needs to be moved to create a three dimensional image and, in some instances, a two dimensional image when the sensing device 34 is a US transducer formed of a one dimensional array of transducer elements.

A tissue-pressure device 34, 46 (e.g., a US transducer array) of the elasticity imaging modality 32 applies pressure to the target and/or the OARs. It is contemplated that the tissue-pressure device 34, 46 can mechanically apply pressure to the target and/or the OARs using, for example, a robotic arm. When the elasticity imaging modality 32 includes the sensor-positioning device 46, the tissue-pressure device 34, 46 can be formed of the sensor-positioning device 46 and the sensing device 34, and apply pressure to the target and/or the OARs via the sensing device 34. For example, the sensor-positioning device 46 can move the sensing device 34 to compress the target and/or the OARs. It is also contemplated that the tissue-pressure device 34, 46 can acoustically apply pressure to the target and/or the OARs. When the sensing device 34 is a US transducer, the sensing device 34 can be employed to acoustically apply pressure to the target and/or the OARs.

During the acquisition of spatially encoded data, the elasticity imaging system 36 controls one or more of the sensing device 34, the sensor-positioning device 46, and the tissue-pressure device 34, 46. In that regard, the elasticity imaging system 36 controls the tissue-pressure device 34, 46 to appropriately apply pressure to the target and/or the OARs when acquiring spatially encoded data for an elasticity image. For example, the elasticity imaging system 36 can control the tissue-pressure device 34, 46 according to an acoustic radiation force impulse (ARFI) imaging technique. Further, where the elasticity imaging modality 32 includes the sensor-positioning device 46, the elasticity imaging system 36 controls the sensor-positioning device 46 to appropriately move the sensing device 34 when generating spatially encoded data for an elasticity image. Even more, the elasticity imaging system 36 can control the sensor-positioning device 46 and/or the tissue-pressure device 34, 46 to ensure the therapy beam is not obstructed by, for example, the sensing device 34. Similarity, the optimization module 24 can generate the treatment plan using the known location and/or motion pattern of the sensing device 34 to ensure the therapy beam is not obstructed.

Where the elasticity imaging modality 32 includes the sensor-positioning device 46 and/or the tissue-pressure device 34, 46 mechanically applies pressure to the target and/or the OARs, the elasticity imaging system 36 can track the motion of the sensor-positioning device 46 and/or the motion of the tissue-pressure device 34, 46 to ensure the correct motion of the sensing device 34 and/or application of force. Further, the optimization module 24 can determine the location of the sensor-positioning device 46 to ensure the therapy beam is not obstructed. The motion is typically tracked using an optical tracker 48, but other devices for tracking are contemplated.

A controller 49 of the elasticity imaging system 36 controls the constituent components of the elasticity imaging system 36, such as the transmitter 45, to carry out the above described functionality. For example, the controller 49 controls the constituent components to generate the elasticity images. To do so, the controller includes at least one memory and at least one processor. The memory includes processor executable instructions embodying the above described functionality of the elasticity imaging system 36, and the processor executes the processor executable instructions.

In addition to, or as an alternative to, receiving the planning image and generating and/or updating the treatment plan based on the planning image, the planning system 18 receives one or more elasticity images from the elasticity imaging modality 32 and updates the treatment plan based on the elasticity images. Typically, the updating entails updating the margins of the treatment plan, but other updates are contemplated. Elasticity images are suitable for updating the margins of the treatment plan since elasticity images can illustrate radiation-related changes to the target, such as size reduction, as the treatment plan is executed. Elasticity images can capture radiation-related change since ionizing radiation is known to change the levels of hemoglobin and water content in the irradiated regions, thereby changing the mechanical properties of the irradiated regions.

To update the treatment plan, the patient 14 is set-up on a treatment couch 50 of a therapy delivery apparatus 52 before beginning therapy delivery. An elasticity module 54 of the planning system 18 then receives an elasticity image (hereafter the "initial elasticity image"), such as a three-dimensional elasticity image, of the target and/or the OARs from the elasticity imaging modality 32. The initial elasticity image provides baseline elastic modulus variations for the target and surrounding normal tissue. Further, the target is delineated in the initial elasticity image using the segmentation module 20 of the planning system 18 to create an initial segmentation.

Thereafter, during therapy delivery and/or between treatment fractions, the elasticity module 54 receives elasticity images from the elasticity imaging modality 32. As to receiving during therapy delivery, elasticity images can be received periodically at a rate determined by an operator of the planning system 18. The elasticity images are suitably of the same type as the initial elasticity image. Upon receiving one of the elasticity images, the target is delineated in the elasticity image using the segmentation module 20 of the planning system 18 to create a current segmentation. It is contemplated that the segmentation module 20 can be employed to create the current segmentation by updating the initial segmentation based on changes in target position.

Having determined the current segmentation, the elasticity module 54 compares the target, as identified by the current segmentation, with the target, as identified by the initial segmentation. Based on this comparison, a determination is made as to whether the target is shrinking and/or otherwise changing in size. Typically, intra-fraction elasticity imaging can reveal real-time changes occurring in the target due to therapy delivery, and inter-fraction elasticity imaging can reveal target shrinkage (if any). If the target is deemed to have shrunk or otherwise changed in size, the margins of the treatment plan can be adjusted accordingly and the treatment plan can be re-optimized using the optimization module 24 of the planning system 18.

The elasticity module 54 can also be employed for determining a delivered dose distribution for the target and and updating the treatment plan based on the delivered dose distribution. This includes determining a cumulative motion pattern, such as a probability density function, of the target for each of the completed fractions of the treatment plan. A cumulative motion pattern for a fraction is determined by accumulating the locations of the target, as determined by the current segmentation, in the elasticity images received during the fraction. The more elasticity images that are received during the fraction, the more accurate the cumulative motion pattern.

The determined cumulative motion patterns are then convolved with corresponding planned dose distributions. For example, a cumulative motion pattern for a fraction is convolved with the planned dose distribution for the fraction. The motion compensated dose distributions are then accumulated to get the delivered dose distribution. Further, the delivered dose distribution is provided to the optimization module 24 of the planning system 18 and the treatment plan is re-optimized based on the delivered dose distribution.

At a scheduled day and time for a therapy session of the patient 14, the therapy delivery apparatus 52 of the therapy system 10, such as a linear particle accelerator, delivers therapy, such as ablation therapy, external beam radiation therapy and/or brachytherapy, to the patient 14. The therapy typically includes radiation, such as one or more of x-rays, protons, high-intensity focused ultrasound (HIFU), and the like. The therapy delivery apparatus 52 is controlled by a delivery control system 56 of the therapy system 10 in accordance with the treatment plan, optionally as updated between fractions and/or during fractions. The treatment plan can be received from, for example, the treatment plan memory 30.

A segmentation module 58 of the delivery control system 56 (or the elasticity imaging system 36) receives an elasticity image of the target and/or the OARs from the elasticity imaging modality 32 and delineates the target in the elasticity image. The target is typically delineated with contour (s) tracing the boundary of the target in the elasticity image. Delineation can be performed automatically and/or manually. As to automatic delineation, any number of known segmentation algorithms can be employed. Alternatively, a registration map between the elasticity image and the planning image can be generated using any number of known registration algorithms, such as deformable image registration algorithms. The delineation of the target in the planning image can then be mapped to the elasticity image using the registration map. As to manual delineation, the segmentation module 58 cooperates with a user interface module 60 of the delivery control system 56 to allow clinicians to manually delineate the target in the elasticity image and/or manually adjust an automatic delineation of the target in the elasticity image.

The user interface module 60 presents a user interface to an associated user with a display device 62 of the delivery control system 56. The user interface allows the user to at least one of delineate the target in the elasticity image, modify a delineation of the target in the elasticity image, and view a delineation of the target in the elasticity image. Typically, the user delineates the target by drawing a contour along the boundary of the target on the elasticity image using a user input device 64 of the delivery control system 56. Further, a delineation is typically viewed by overlaying a representative contour on the elasticity image, and modified by resizing and/or reshaping the representative contour using the user input device 64.

Before beginning therapy delivery, the patient is set-up on the treatment couch 50 of the therapy delivery apparatus 52. An elasticity image (hereafter the "initial elasticity image"), such as a three-dimensional elasticity image, or other position indicating data of the target and/or the OARs is then received from the elasticity imaging modality 32. Further, the target is delineated in the initial elasticity image using the segmentation module 58 to create an initial segmentation, and the margins of the treatment plan are combined with the initial segmentation to identify the planning target volume in the initial elasticity image.

During therapy delivery, a gating module 66 of the delivery control system 56 receives a series of elasticity images, such as three-dimensional elasticity images, of the target from the elasticity imaging modality 32 or other measures of target location. For example, the elasticity images can be received periodically at a rate determined by an operator of the delivery control system 56. The periodicity is selected to be short relative to anticipated patient motion (e.g., short compared to the respiratory cycle). The elasticity images are suitably of the same type as the initial elasticity image. Upon receiving an elasticity image, the target is delineated in the elasticity image using the segmentation module 58 of the delivery control system 56 to create a current segmentation. It is contemplated that the segmentation module 58 can be employed to create the current segmentation by updating the initial segmentation based on changes in target position. Alternatively, the elasticity imaging system 36 can be used to measure changes in distance or location of the target relative to the sensing device 34, for example, operating in the ARFI mode.

Having determined the current segmentation, the gating module 66 compares the location of the target, as identified by the current segmentation, with the location of the planning target volume, as identified in the initial elasticity image. Based on this comparison, a decision is made as to whether to turn the therapy beam OFF or keep it ON. Typically, the decision criterion differs based on clinical needs. However, one example is to turn the therapy beam OFF if there is less than 90% overlap between the planning target volume and the target; otherwise, the beam may be kept ON.

The planning system 18 and the delivery control system 56 include one or more memories 68, 70 and one or more processors 72, 74. The memories 68, 70 store processor executable instructions for carrying out the functions associated with the planning system 18 and the delivery control system 56, including those associated with the segmentation modules 20, 58, the user interface modules 22, 60, the optimization module 24, the elasticity module 54, and the gating module 66. The processors 72, 74 execute the processor executable instructions stored on the memories 68, 70. The planning system 18 and/or the therapy control system 56 further include one or more system buses 76, 78 facilitating communication between the processors 72, 74, the memories 68, 70, the user input devices 28, 64 and the display devices 26, 62.

Figure 2:
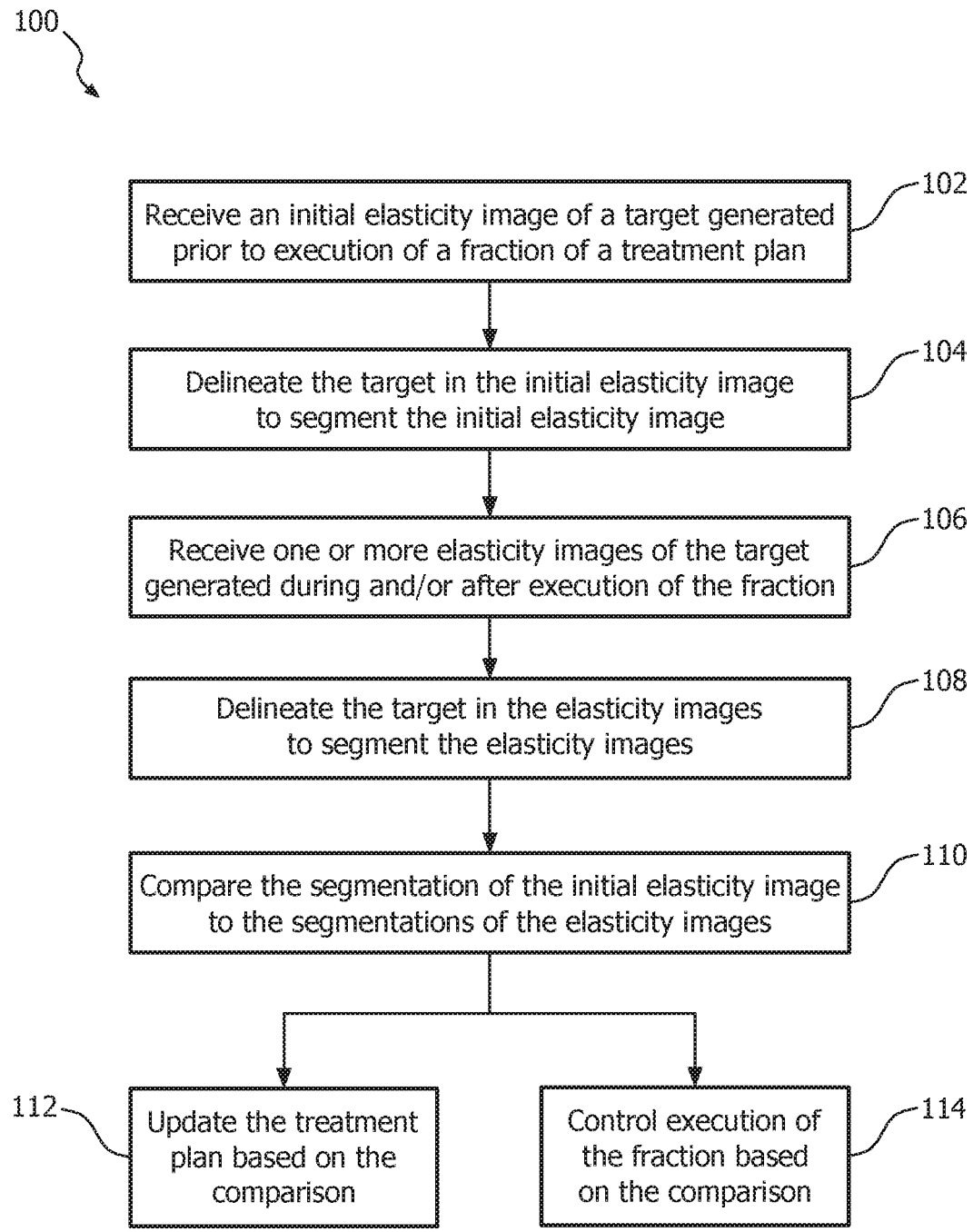
FIG. 2 illustrates a block diagram of a method for treating a target of a patient.

With reference to FIG. 2, a block diagram of a therapy method 100 for treating the target is provided. The processors 72, 74 of the planning system 18 and the delivery control system 56 suitably perform the method 100. The method 100 includes receiving 102 an initial elasticity image of the target from the elasticity imaging modality 32. The initial elasticity image is generated prior to execution of a fraction of the treatment plan, typically once the patient 14 has been aligned on the treatment couch 50 of the therapy delivery apparatus 52 for the fraction. The target is then delineated 104 in the initial elasticity image using the segmentation modules 20, 58 to segment the initial elasticity image. One or more elasticity images of the target are then received 106. The elasticity images are generated during and/or after execution of the fraction, but typically prior to execution of the next fraction. The target is then delineated 108 in the elasticity images using the segmentation modules 20, 58 to segment the elasticity images. The segmentation of the initial elasticity image is compared 110 against the segmentations of the elasticity images to identify motion of the target and/or changes of the target. Based on the comparison, the treatment plan is updated 112 and/or execution of the fraction is controlled 114. The updating 112 includes, for example, updating margins of the treatment plan, and the controlling 114 includes, for example, gating the therapy beam.

It is to be appreciated that the concepts of the present disclosure as applied to therapy delivery are severable from the concepts of the present disclosure as applied to planning. For example, dynamic gating as described herein can be used independent of dynamic margin adjustment. Also, the planning system 18 and the delivery control system 56 can be combined into a common system.

Even more, it is to be appreciated that the concepts of the present disclosure can improve the efficiency of therapy delivery gating. This is achieved by directly utilizing positional information of the target instead of using external or internal surrogates for target motion. The positional information of the target can be determined from real-time elasticity images (independently or as a complement to other types of images), which are known to image cancerous tumors with high contrast.

Further, it is to be appreciated that the concepts of the present disclosure can reduce unnecessary harmful dose to normal tissue surrounding the target. This is achieved by dynamically adjusting the margins in-between and/or during fractions. If target shrinkage is observed in response to therapy delivery, the treatment plan can be made to account for this change in the target shape and size.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes at least one memory and at least one processor, the processor executing processor executable instructions on the memory; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A therapy planning method comprising:
   executing the fraction of the treatment plan for the target, the fraction specifying beam directions and energies for treating the target;
   receiving initial elasticity data indicative of a location of the target generated prior to the execution of a fraction of a treatment plan for the target;
   receiving additional elasticity data indicative of a location of the target generated during or after the execution of the fraction;
   comparing the initial elasticity data and the additional elasticity data to identify at least one of motion of the target and changes of the target; and,
   based on the comparison, at least one of:
   updating the treatment plan; and
   controlling the execution of the fraction.

2. The therapy planning method according to claim 1, further including:
   delineating the target in the initial elasticity image to segment the initial elasticity image;
   delineating the target in the additional elasticity images to segment the additional elasticity images;
   comparing the segmentation of the initial elasticity image against the segmentations of the additional elasticity images.

3. The therapy planning method according to claim 1, further including:
   updating planning target volume (PTV) margins of the treatment plan based on the comparison, the updated PTV margins employed by one or more subsequent fractions of the treatment plan.

4. The therapy planning method according to claim 1, further including:
   gating a therapy beam treating the target during the execution of the fraction based on the comparison.

5. The therapy planning method according to claim 1, wherein the initial elasticity data and the additional elasticity data are generated by an ultrasound imaging modality, and wherein the initial elasticity data and the additional elasticity data include three-dimensional images of the target.

6. The therapy planning method according to claim 1, wherein the initial elasticity data and the additional elasticity data are generated from spatially encoded data generated by a sensing device, the sensing device moved by a sensor-positioning device during acquisition of the spatially encoded data.

7. The therapy planning method according to claim 6, wherein the sensor-positioning device moves the sensing device during acquisition of the spatially encoded data to apply varying degrees of pressure on the target and surrounding normal tissue.

8. At least one processor programmed to perform the therapy planning method according to claim 1.

9. A non-transitory computer readable medium carrying software which controls at least one processor to perform the therapy planning method according to claim 1.

10. The therapy planning method according to claim 1, including updating the treatment plan based on the comparison.

11. The therapy planning method according to claim 1, including receiving the additional elasticity data indicative of the location of the target generated during the execution of the fraction and controlling the execution of the fraction based on the comparison.

12. The therapy planning method according to claim 11, wherein:
- the receiving of the additional elasticity data indicative of the location of the target generated during the execution of the fraction includes receiving elasticity images periodically and delineating the target in the elasticity images;
- the comparison includes determining an overlap between the target delineated in the elasticity images and the location of the target generated prior to the execution of the fraction; and
- the controlling of the execution of the fraction based on the comparison includes gating a therapy beam treating the target during the execution of the fraction based on the determined overlap.

13. The therapy planning method according to claim 12, wherein the gating of the therapy beam includes turning the therapy beam off.

* * * * *